United States Patent [19]
Tanaka et al.

[11] Patent Number: 4,465,480
[45] Date of Patent: Aug. 14, 1984

[54] BLOOD TRANSFUSION TUBES AND DEVICES FOR USE IN CONTACT WITH HUMAN BLOOD

[75] Inventors: Masakazu Tanaka; Ken Murayama, both of Ootsu, Japan

[73] Assignee: Toyo Boseki Kabushiki Kaisha, Osaka, Japan

[21] Appl. No.: 333,186

[22] Filed: Dec. 21, 1981

[30] Foreign Application Priority Data

Sep. 2, 1981 [JP] Japan ................................ 56-138734

[51] Int. Cl.³ .............................................. A61M 5/00
[52] U.S. Cl. ........................................... 604/264; 3/1; 604/403; 128/335.5
[58] Field of Search ............... 128/130, 132 D, 132 R, 128/155, 156; 3/1, 1 A, 1 R; 560/157; 604/264, 403, 408

[56] References Cited

U.S. PATENT DOCUMENTS 3,822,238  7/1974  Blair et al. .................... 3/1
4,049,591  9/1977  McEntire et al. ............ 560/157
4,131,604  12/1978  Szycher ........................ 3/1 A
4,173,689  11/1979  Lyman et al. ................ 3/1 A
4,255,550  3/1981  Gould ........................... 128/132 D

FOREIGN PATENT DOCUMENTS 50-16800  2/1975  Japan.

OTHER PUBLICATIONS

Makromol. Chem. 179, 1121-1124 (1978).
ANSI/ASTM D 1708-1779.
J. Biomed. Mater. Res. Symposium No. 3, pp. 129-154.
J. Biomed. Mater. Res. vol. 2, pp. 121-130 (1968).
Synthetic Biomedical Polymers Concepts and Applications, edited by M. Szycher and W. J. Robinson.

Primary Examiner—Benjamin R. Padgett
Assistant Examiner—T. J. Wallen
Attorney, Agent, or Firm—Wenderoth, Lind & Ponack

[57] ABSTRACT

Devices such as blood transfusion tubes, which can be contacted with human blood at reduced risk of blood clotting, made of a segmented polyether polyurethane urea obtained by chain extending an isocyanate-terminated prepolymer with a diamine having a branch at at least one α-carbon atom, such as 1,2-propylene diamine or 1,4-cyclohexylene diamine.

5 Claims, No Drawings

BLOOD TRANSFUSION TUBES AND DEVICES FOR USE IN CONTACT WITH HUMAN BLOOD

The present invention relates to blood transfusion tubes, or devices for use in direct or indirect contact with human blood, consisting of or coated with an anti-thrombogenic polymer.

The object of the present invention is to provide blood transfusion tubes, or devices for use in direct or indirect contact with human blood which are able to prevent or remarkably delay blood clotting without particular use of an anticoagulant.

In recent years, high polymer materials have been used for artificial organs such as artificial kidneys, artificial lungs, circulatory assist devices, artificial blood vessels, etc. and for many medical appliances such as injectors, blood bags, cardinal catheters, etc. However, one of the great problems concerned with them is that the high polymer materials cause various undesirable biological interactions of biological systems with foreign surfaces, and in the case of their contact with blood, they bring about blood clotting, thus causing various disturbances.

Various attempts have been made to prevent such clotting, such as the use of silicone resins, segmented polyether polyurethane ureas, polysiloxane-polyurethane block copolymers, etc.

Silicone resins are problematic in antithrombogenicity and in strength of material, and polysiloxanepolyurethane block copolymers are excellent in antithrombogenicity, but to have problems in strength of material.

The excellence in antithrombogenicity of segmented polyurethanes is already known in this field of industry. For example, in Laid-Open Japanese Patent Application (Patent Kokai) No. 16800/1975, it is described that a thermoplastic polytetramethylene ether polyurethane urea resin obtained by chain-extension of a prepolymer having a number average molecular weight of about 2,000 to 10,000 (obtained by reacting a polytetramethylene glycol having a molecular weight of from 650 to 2,000 with 4,4'-diphenylmethane diisocyanate in a molar ratio of from 1:1.3 to 1:1.7) by means of water, if desired in the presence of a small quantity of a chain reaction stopper, has antithrombogenicity. But, for such a polyether polyurethane urea chain-extended by means of water, there is a fear of its toxicity to cells because of an aromatic amine produced by the reaction of water and the aromatic isocyanate; in comparison with a polyether polyurethane urea chain-extended by means of an aliphatic primary diamine, it has a better antithrombogenicity, but when it is used as a material for an artificial heart, there is a problem in that it does not have long-term antithrombogenicity; and in addition, it has a poor processability because of a large surface frictional coefficient due to its having an aromatic urea bond.

We, the inventors, have studied intensively to obtain a material which is excellent in antithrombogenicity, non-toxic, and excellent in processability, and have found that polyether polyurethane ureas composed of the following particular composition are very suitable for such properties. The present invention is based on this discovery.

Thus, the present invention provides blood transfusion tubes, or devices for use in direct or indirect contact with human blood, consisting of or coated with a segmented polyether polyurethane urea obtained by chain-extension of an isocyanate-terminal prepolymer (obtained by reacting a polyoxyalkylene diol having a molecular weight of from 650 to 3,000 with a diisocynate) with a diamine represented by the following general formula (I) or/and a diamine represented by the following general formula (II):

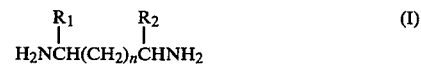

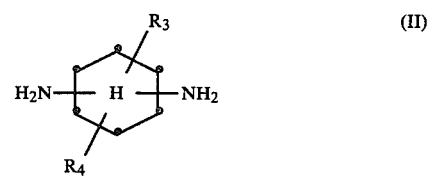

wherein each of $R_1$ and $R_2$ is an alkyl group having 1 to 5 carbon atoms, or one of $R_1$ and $R_2$ is a hydrogen atom and the other is an alkyl group having 1 to 5 carbon atoms, each of $R_3$ and $R_4$ is a hydrogen atom or an alkyl group having 1 to 5 carbon atoms, and n represents 0 or an integer from 1 to 4.

The blood transfusion tubes in the present invention are tubes for transfusion of blood, and their diameter, thickness and length are not critical.

The devices for use in direct or indirect contact with human blood mean medical appliances which treat blood, such as artificial hearts, artificial lungs, artificial kidneys, circulatory assist devices, artificial valves, artificial blood vessels, blood bags, cannulae, shunts, blood circulatory devices, various catheters, etc. which are well known per se.

For the blood transfusion tubes, or devices for use in direct or indirect contact with human blood of the present invention, there is used a segmented polyether polyurethane urea chain-extended with a diamine represented by the general formula (I) or (II), having a branch at at least one α-positon carbon atom, and this polymer is characterized by its excellence in antithrombogenicity, processability, solubility in solvents, and mechanical properties. In the case of conventional polyether polyurethane chain-extended by means of low molecular diols, no urea bonds come to exist, but the stability to hydrolysis and the mechanical properties are remarkably lowered, so that they are not suitable for long term use in living bodies, whereas the materials of the present invention have no such defects. Also, in the case of polyether polyurethane ureas for which a diamine is used, for example ethylene diamine, having no branch at the α-position carbon atom, the antithrombogenicity is lowered in comparison with those of the present invention.

As the polyoxyalkylene diols having a molecular weight of from 650 to 3,000, there can be mentioned polytetramethylene glycol, polypropylene glycol, etc. having a molecular weight of from 650 to 3,000, preferably from 800 to 2,000.

A polyoxyalkylene glycol, one terminal of which is blocked, represented by the following general formula (III) may exist in the prepolymer reaction stage in a quantity of from 0.2 to 10 mol % (preferably from 0.5 to 7 mol %) based on the diisocyanate component:

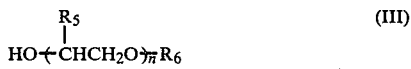

wherein $R_5$ is a hydrogen atom or methyl group, $R_6$ is an alkyl group having 1 to 20 carbon atoms, aralkyl group, phenyl group, or substituted phenyl group, and n is an integer of from 20 to 500.

As the diisocyanate, there can be mentioned aromatic diisocyanate such as 2,4-toluene diisocyanate, 2,6-toluene diisocyanate or a mixture of these two diisocyanates, xylylene diisocyanate, 4,4'-diphenylmethane diisocyanate, 4,4'-diphenylpropane diisocyanate, phenylene diisocyanate, naphthalene diisocyanate, etc. and particularly 4,4'-diphenylmethane diisocyanate is preferable.

As concrete examples of the diamines represented by the general formula (I), there can be mentioned 1,2-propylene diamine, 1,2-butylene diamine, 1,3-butylene diamine, 2,3-butylene diamine, 1,2-pentylene diamine, 1,3-pentylene diamine, 2,3-pentylene diamine, 2,4-pentylene diamine, 1,2-hexylene diamine, 1,3-hexylene diamine, 1,4-hexylene diamine, 2,5-hexylene diamine, 1,2-heptylene diamine, 1,3-heptylene diamine, 1,5-heptylene diamine, 1,6-heptylene diamine, 2,6-heptylene diamine, etc.

As concrete examples of the diamines represented by the general formula (II), there can be mentioned 1,4-cyclohexylene diamine, 1,2-cyclohexylene diamine, 1,3-cyclohexylene diamine, 2-methyl-1,4-cyclohexylene diamine, 3-methyl-1,4-cyclohexylene diamine, etc. particularly preferable is 1,2-propylene diamine.

The segmented polyether polyurethane urea is produced by reacting the above-mentioned polyoxyalkylene diol and diisocyanate in a molar ratio of from 1:1.3 to 1:3.0, preferably in a molar ratio of from 1:1.5 to 1:2.5 to synthesize a prepolymer having an isocyanate group at each terminal; dissolving the prepolymer in a solvent, such as dimethylformamide or dimethylacetamide, which does not react with isocyanate groups; chain-extending the prepolymer by means of a diamine represented by the general formula (I) or/and a diamine represented by the general formula (II), adding, if necessary, a primary or secondary monoamine, or a monohydroxy low molecular weight alcohol, and then stopping the reaction. If necessary, less than 20 mol % of the diamines of the present invention may be replaced with other diamines.

The segmented polyether polyurethane urea obtained by the above-mentioned method is formed into blood transfusion tubes, or devices for use in direct or indirect contact with human blood of various shapes as mentioned above, by itself by a known method such as a dipping method, or by coating a base material.

The segmented polyether polyurethane urea of the present invention has excellent antithrombogenicity and at the same time it is also excellent in processability, solubility in solvents and mechanical properties, so that the blood transfusion sets, or the devices for use in direct or indirect contact with human blood produced therefrom, for example artificial hearts, artificial lungs, artificial kidneys, circulatory assist devices, artificial valves, artificial blood vessels, blood bags, cannulae, shunts, blood circulatory devices, various catheters, etc. are very useful in comparison with those produced from conventional high polymer materials.

The following examples explain, the present invention concretely. In the examples, parts mean parts by weight.

The evaluation of antithrombogenicity was carried out be referring to the column method (Makromol. Chem. 179,1121 (1978)) developed by Sakurai et al.

That is to say, glass beads of 200 μ diameter are coated with a polymer. 0.5 g of the beads are packed to the closest possible density into 5 cm of a vinyl chloride tube of 0.3 mm inner diameter equipped with a cock at each end, and then the tube is filled with physiological saline solution. 2 ml of fresh blood is collected from the jugular vein of an adult dog by means of a disposable injector for medical use having 10 ml capacity. The injector is immediately set to a syringe pump which is able to extrude at a constant flow rate. To the tip of the injector from which the injector needle has been removed, the previously prepared beads-packed column is connected. The blood is made to flow at a flow rate of 1.0 ml/min for one minute. The blood which has passed through the column is collected into a commercially available sampling bottle, the inner surface of which is covered with an anticoagulant EDTA. The number of platelets in the blood which has passed through the column is calculated by the Brecher Cronkite method. The number of platelets adhered is the value obtained by subtracting the number of platelets after passing through the column from the number of platelets before passing through the column.

The relative comparison of the number of platelets between polymeric materials is obtained as follows. The smaller this value, the smaller the adhesive properties of the platelets, that is, the better the antithrombogenicity.

$$\text{Relative adhesion value} = \frac{\text{Number of platelets adhered to high polymer-coated beads}}{\text{Number of platelets adhered to non-coated glass beads}}$$

REFERENTIAL EXAMPLE 1

1360 parts of polytetramethylene glycol having a number average molecular weight of 1360 and 500 parts of 4,4'-diphenylmethane diisocyanate were reacted under stirring at 70° C. in a stream of nitrogen for 30 minutes, to synthesize an isocyanate-terminated prepolymer. Thereafter, 7000 parts of dimethylformamide (hereinafter abbreviated as DMF) was added to dissolve the prepolymer. This solution was cooled to 8° C., and to this solution a solution of 67 parts of 1,2-propylenediamine dissolved in 608 parts of DMF was added dropwise in one hour. After the addition was complete, the solution was stirred at room temperature for 30 minutes, and a solution of 12.9 parts of dibutylamine dissolved in 50 parts of DMF was added. After stirring for 30 minutes, a solution of 10.2 parts of acetic anhydride dissolved in 50 parts of DMF was added. After stirring for 30 minutes, the reaction was caused to stop, to obtain a solution of segmented polyether polyurethane urea having a dope concentration of 20% and a viscosity of 700 poises (30° C.).

By diluting this polymer solution with DMF, a 0.1 weight % solution was produced. In this solution glass beads were immersed, and then the beads were dried so that the polymer was coated the surface of the beads. Using the resin-coated glass beads produced in this way, the evaluation of antithrombogenicity was carried out.

The tensile strength was measured in accordance with ASTM D-1708. The results of the tests of antithrombogenicity and tensile strength are shown in Table 1.

REFERENTIAL EXAMPLE 2

1100 parts of polytetramethylene glycol having a number average molecular weight of 1100 and 500 parts of 4,4'-diphenylmethane diisocyanate were reacted under stirring at 65° C. in a stream of nitrogen for 45 minutes, to synthesize an isocyanate-terminated prepolymer. Thereafter, 5800 parts of DMF was added to dissolve the prepolymer. This solution was cooled to 8° C., and to this solution, a solution of 70.4 parts of 1,2-propylenediamine dissolved in 800 parts of DMF was added dropwise in one hour. After the addition was complete, the solution was stirred at room temperature for 30 minutes, and then a solution of 6.5 parts of dibutylamine dissolved in 50 parts of DMF was further added. After stirring for 30 minutes, the reaction was caused to stop to obtain a solution of segmented polyether polyurethane urea having a dope concentration of 20% and a viscosity of 730 poises.

Various tests were carried out in the same way as in Referential Example 1. The results of the tests of antithrombogenicity and tensile strength are shown in Table 1.

REFERENTIAL EXAMPLE 3

850 parts of polytetramethylene glycol having a number average molecular weight of 850 and 500 parts of 4,4'-diphenylmethane diisocyanate were reacted under stirring at 65° C. in a stream of nitrogen for 30 minutes, to synthesize an isocyanate-terminated prepolymer. Thereafter, 4800 parts of DMF was added to dissolve the prepolymer. This solution was cooled to 8° C., and to this solution, a solution of 70.4 parts of 1,2-propylenediamine dissolved in 800 parts of DMF was added dropwise in one hour. After the addition was complete, the solution was stirred at room temperature for 30 minutes, and a solution of 6.5 parts of dibutylamine dissolved in 50 parts of DMF was added. After stirring for 30 minutes, a solution of 5.1 parts of acetic acid anhydride dissolved in 50 parts of DMF was further added. After stirring for 30 minutes, the reaction was caused to stop to obtain a solution of segmented polyether polyurethane urea having a dope concentration of 20% and a viscosity of 770 poises (30° C.).

In the same way as in Referential Example 1, various tests were carried out. The results of the tests of antithrombogenicity and tensile strength are shown in Table 1.

REFERENTIAL EXAMPLE 4

2050 parts of polytetramethylene glycol having a number average molecular weight of 2050 and 500 parts of 4,4'-diphenylmethane diisocyanate were reacted under stirring at 70° C. in a stream of nitrogen for 60 minutes, to synthesize an isocyanate-terminate prepolymer. Thereafter, 9608 parts of DMF was added to dissolve the prepolymer. This solution was cooled to 8° C. and to this solution, a solution of 70.4 parts of 1,2-propylenediamine dissolved in 800 parts of DMF was added dropwise in one hour. After the addition was complete, the solution was stirred at room temperature for 30 minutes, and a solution of 6.5 parts of dibutylamine dissolved in 50 parts of DMF was added. After stirring for 30 minutes, a solution of 5.1 parts of acetic acid anhydride dissolved in 50 parts of DMF was further added. After stirring for 30 minutes, the reaction was caused to stop to obtain a solution of segmented polyether polyurethane urea having a dope concentration of 20% and a viscosity of 680 poises (30° C.).

In the same way as in Referential Example 1, various tests were carried out. The results of the tests of antithrombogenicity and tensile strength are shown in Table 1.

REFERENTIAL EXAMPLE 5

2050 parts of polytetramethylene glycol having a number average molecular weight of 2050 and 500 parts of 4,4'-diphenylmethane diisocyanate were reacted under stirring at 70° C. in a stream of nitrogen for 60 minutes to synthesize an isocyanate-terminated prepolymer. Thereafter, 9568 parts of dimethylacetamide (hereinafter abbreviated as DMAC) was added to dissolved the prepolymer. This solution was cooled to 8° C. and to this solution, a solution of 54.1 parts of ethylenediamine dissolved in 800 parts of DMAC was added dropwise in one hour. After the addition was complete, the solution was stirred at room temperature for 60 minutes, and a solution of 12.9 parts of dibutylamine dissolved in 50 parts of DMAC was added. After stirring for 30 minutes, a solution of 10.2 parts of acetic acid anhydride dissolved in 50 parts of DMF was further added. After stirring for 30 minutes, the reaction was caused to stop to obtain a solution of segmented polyether polyurethane urea having a dope concentration of 20% and a viscosity of 550 poises (30° C.).

In the same way as in Referential Example 1, various tests were carried out. The results of the tests of antithrombogenicity and tensile strength are shown in Table 1.

REFERENTIAL EXAMPLE 6

2050 parts of polytetramethylene glycol having a number average molecular weight of 2050, 500 parts of 4,4'-diphenylmethane diisocyanate, 880 parts of DMAC and 7.2 parts of water were reacted under stirring at 40° C. in a stream of nitrogen for 45 minutes to synthesize an isocyanate-terminated prepolymer. Thereafter, 8683 parts of DMAC was added to dissolve the prepolymer. This solution was cooled to 8° C., and to this solution, a solution of 44.8 parts of ethylenediamine dissolved in 800 parts of DMAC was added dropwise in one hour. After the addition was complete, the solution was stirred at room temperature for 30 minutes and a solution of 5.2 parts of dibutylamine dissolved in 100 parts of DMAC was added. After stirring for 30 minutes, a solution of 4.1 parts of acetic acid anhydride dissolved in 50 parts of DMAC was further added. After stirring for 30 minutes, the reaction was caused to stop to obtain a solution of segmented polyether polyurethane urea having a dope concentration of 20% and a viscosity of 810 poises (30° C.).

In the same way as in Referential Example 1, various tests were carried out. The results of the tests of antithrombogenicity and tensile strength are shown in Table 1.

TABLE 1

Results of the evaluation of antithrombogenicity and tensile strength

| Sample | Relative adhesion value (that of glass taken as 1.0) | Tensile strength kg/mm² |
|---|---|---|
| Referential Example 1 (present invention) | 0.32 | 5.25 |
| Referential Example 2 (present invention) | 0.39 | 5.38 |
| Referential Example 3 (present invention) | 0.42 | 5.48 |
| Referential Example 4 (present invention) | 0.40 | 4.82 |
| Referential Example 5 (comparative example) | 0.50 | 4.40 |
| Referential Example 6 (comparative example) | 0.65 | 4.25 |
| Polyurethane-silicone block copolymer (an existing product) | 0.75 | 1.94 |

EXAMPLE 1

Using the polymer solution obtained in Referential Example 1, an artificial heart pump of diaphragm type was produced. When this heart pump was equipped for a calf having a weight of 65 kg as a total artificial heart, it worked very satisfactorily. After three weeks, the artificial heart was taken out, and formation of any thrombosis was minutely examined. No formation of thrombosis was observed at all.

EXAMPLE 2

The inner side of a commercially available polyvinyl chloride tube (inner diameter: 5 mm) for use as a blood circulatory device was coated with the polymer solution obtained in ReferentiAl Example 2. This tube was tested as the blood circulatory device of an artificial kidney of a mongrel dog (weight: 10 kg). The result was that this blood circulatory device could be used very satisfactorily for a long time without any coagulation of blood, variation of its concentration, etc.

EXAMPLE 3

A catheter of 2 mm outer diameter was produced by dry-process formation from the polymer solution obtained in Referential Example 4. This catheter was compared with a catheter made of polyvinyl chloride. It was found that the former worked very satisfactorily without any formation of thrombosis.

EXAMPLE 4

1360 parts of polytetramethylene glycol having a number average molecular weight of 1360, 300 parts of polyethylene glycol having a number average molecular weight of 6000, one terminal of which is blocked with a phenyl group, and 500 parts of 4,4'-diphenylmethane diisocyanate were reacted under stirring at 70° C. in a stream of nitrogen to synthesize an isocyanate-terminated prepolymer. Thereafter, 7929 parts of DMF was added to dissolve the prepolymer. This solution was cooled to 8° C., and to this solution, a solution of 72.3 parts of 1,2-propylenediamine dissolved in 950 parts of DMF was added dropwise in one hour. After the addition was complete, the solution was stirred for 30 minutes at room temperature, and then a solution of 1.0 part of acetic acid anhydride dissolved in 50 parts of DMF was added. After stirring for 30 minutes, the reaction was caused to stop to obtain a solution of segmented polyether polyurethane urea having a dope concentration of 20% and a viscosity of 630 poises. In the same way as in Example 1, this solution was made into a film having a thickness of 50 μ. Using this film and in the same way as in Example 1, the thrombogenicity was evaluated. The results are shown in Table 2.

TABLE 2

| Sample | Relative adhesion value (that of glass taken as 1.0) |
|---|---|
| Example 4 | 0.30 |
| Silicone resin for medical use | 0.57 |

What we claim is:

1. A device for use in contact with human blood, consisting of or covered with a segmented polyether polyurethane urea obtained by chain-extension of an isocyanate-terminated prepolymer, said prepolymer being obtained by reacting a polyoxyalkylene diol having a molecular weight of from 650 to 3000 with a diisocyanate, said chain-extension being conducted with a diamine represented by the following formula (I) or-/and a diamine represented by the following formula (II):

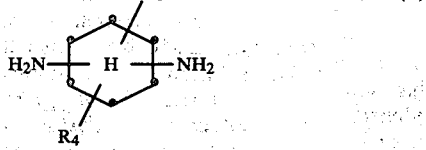

wherein each of $R_1$ and $R_2$ is an alkyl group having 1 to 5 carbon atoms or one of $R_1$ and $R_2$ is a hydrogen atom and the other is an alkyl group having 1 to 5 carbon atoms, each of $R_3$ and $R_4$ is a hydrogen atom or an alkyl group having 1 to 5 carbon atoms, and n represents 0 or an integer from 1 to 4.

2. A device according to claim 1, which is a blood transfusion tube.

3. A device according to claim 1, wherein a polyoxyalkylene glycol, one terminal of which is blocked, represented by the following formula (III), exists in the prepolymer reaction stage in a quantity of from 0.2 to 10 mol %, based on the diisocyanate component:

wherein $R_5$ is a hydrogen atom or methyl group, $R_6$ is an alkyl group having 1 to 20 carbon atoms, aralkyl group, phenyl group, or substituted phenyl group, and n is an integer of from 20 to 500.

4. A device according to claim 3, which is a blood transfusion tube.

5. A device according to claim 3, wherein the quantity of the polyoxyalkylene glycol is 0.5 to 7 mol % based on the diisocyanate component.

* * * * *